United States Patent [19]

Brunelle

[11] Patent Number: 4,460,778

[45] Date of Patent: Jul. 17, 1984

[54] PHASE TRANSFER CATALYSTS

[75] Inventor: Daniel J. Brunelle, Scotia, N.Y.

[73] Assignee: General Electric Company, Schenectady, N.Y.

[21] Appl. No.: 489,690

[22] Filed: Apr. 28, 1983

[51] Int. Cl.$^3$ .......................................... C07D 213/74
[52] U.S. Cl. ..................................... 546/304; 548/486
[58] Field of Search .......................... 546/304; 548/486

[56] References Cited

U.S. PATENT DOCUMENTS 3,852,242  12/1974  White ............................. 260/47 CZ
4,257,953   3/1981  Williams et al. ................ 260/326 R
4,273,712   6/1981  Williams ......................... 260/326 N

FOREIGN PATENT DOCUMENTS 479925   5/1936   United Kingdom .

OTHER PUBLICATIONS

Cheek, et al. "Preparation and Characterization of a Substituted Alkylpyridinium Chloroaluminate Molten Salt System," Inorganic Chemistry vol. 21, Oct. 1982, pp. 3581-3584.

Cas Online TM, Search Statistics-P035038A, American Chemical Society (1983).

Primary Examiner—Henry R. Jiles
Assistant Examiner—Dale A. Bjorkman
Attorney, Agent, or Firm—William A. Teoli; James C. Davis, Jr.; James Magee, Jr.

[57]  ABSTRACT

Branched alkyldiorganoaminopyridinium salts have been found useful as phase transfer catalysts for facilitating nucleophilic aromatic substitution. For example, the 2-ethylhexyl salts of dialkylaminopyridine, can be used as stable phase transfer catalysts for making aromatic etherimides by reacting substituted phthalimides and alkali metal phenoxides in the presence of a nonpolar organic solvent.

4 Claims, No Drawings

PHASE TRANSFER CATALYSTS

CROSS REFERENCE TO RELATED APPLICATIONS

Reference is made to the copending application of Daniel J. Brunelle et al, RD-14532, for Method for Making Aromatic Ethers and Catalysts Used in Such Method, filed concurrently herewith and assigned to the same assignee as the present invention.

BACKGROUND OF THE INVENTION

As shown by Williams, U.S. Pat. No. 4,273,712, and Williams U.S. Pat. No. 4,257,953, assigned to the same assignee as the present invention, methods are provided for making aromatic bis(etherimide)s of the formula,

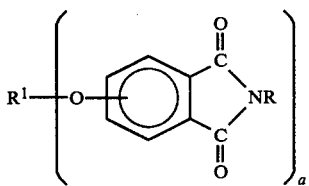

where R is a monovalent radical selected from hydrogen, a $C_{(1-8)}$ alkyl radical and $C_{(6-13)}$ aryl radical, $R^1$ is a $C_{(6-30)}$ aromatic organic radical, and a is an integer equal to 1 or 2, and when a is 1, $R^1$ is monovalent and when a is 2, $R^1$ is divalent. Reaction was effected between a substituted phthalimide of the formula,

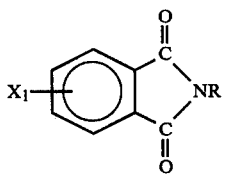

and an alkali metal phenoxide of the formula,

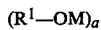

in the presence of a nonpolar organic solvent and a phase transfer catalyst, where R, $R^1$ and a are as previously defined, $X_1$ is a radical selected from nitro and halo, and M is an alkali metal ion.

The phase transfer catalyst utilized by Williams and Williams et al were tetraorgano ammonium or phosphonium salts which allowed for the production of aromatic etherimides in the absence of a dipolar aprotic solvent. Although valuable results are obtained in accordance with the practice of the Williams or Williams et al methods, quaternary ammonium or phosphonium salts are often unstable. As a result, these phase transfer catalysts are often difficult to recycle.

In the copending application of Daniel J. Brunelle et al, Ser. No. 489689, certain diorganoaminopyridinium salts, such as neopentyldialkylaminopyridinium salts, were found to be highly effective phase transfer catalysts. In addition, these diorganoaminopyridinium salts unlike the quaternary ammonium or phosphonium salts of Williams or Williams et al, U.S. Pat. No. 4,273,712 and 4,257,953 are very stable and can be recycled satisfactorily.

As utilized hereinafter, the term "catalyst stability" means the half-life of the catalyst as determined by heating an equal molar amount of phase transfer catalyst and the disodium salt of bisphenol-A in toluene under sealed conditions for a particular period of time which can vary between one-half hour or less to 16 hours or more. Assuming a pseudo-first order for decomposition of the phase transfer catalyst, the amount of catalyst remaining after a certain heating period as determined by NMR analysis can be extrapolated or interpolated to determine the midpoint of the linear plot. This procedure is shown by J. March, "Advanced Organic Chemistry," 2nd Ed., pp. 199-202. This procedure will provide a plot of ln[catalyst] vs. time, should yield a linear plot.

Experience has shown that the half-life or stability of the diorganoaminopyridinium salts, as shown in copending application of Daniel J. Brunelle et al, is about 2 hours, while the half-life of the quaternary ammonium or phosphonium salts can be as little as around 8 minutes. However, as shown by Brunelle et al, maximum stability of the N-alkyldiorganoaminopyridinium salts is achieved by introducing neopentyl functionality onto the diorganoaminopyridinium nucleus. The resulting neopentyldialkylpyridinium salts have been found to have half-lives as high as twelve hours as compared to 8 minutes for the quaternary ammonium or phosphonium salts and 2 hours for the N-linear $C_{(4-12)}$ alkyl diorganoaminopyridinium salts. Although these neopentyldialkylpyridinium salts exhibit a maximum degree of stability, a heating period for several days at 140° C. is required to achieve a satisfactory yield of this phase transfer catalyst.

The present invention is based on my discovery that 2-ethylhexyl salts of dialkylaminopyridine have half-lives as high as eleven hours. Surprisingly, these branched alkyl salts of dialkylaminopyridine, unlike the aforementioned neopentyl dialkylaminopyridinium salts requiring several days to synthesize, can be made at yields exceeding 90%, by stirring a mixture of a dialkylaminopyridine with a 2-ethylhexylalkanesulfonate at 110° C. for only 2 hours. Direct metathesis from the alkylate salt to the halide can be achieved by simply shaking a solution of the salt with a saturated aqueous alkali metal halide solution, followed by drying and evaporation.

STATEMENT OF THE INVENTION

There is provided by the present invention N-2 branched alkyldiorganoaminopyridinium salts of the formula

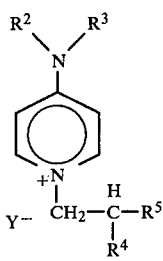

where $R^2$ and $R^3$ are monovalent or divalent organo radicals selected from $C_{(1-13)}$ hydrocarbon radicals and $C_{(1-13)}$ substituted hydrocarbon radicals and $C_{(1-8)}$ divalent alkylene radicals which together can be part of a cyclic structure forming a $C_{(4-12)}$ ring, $R^4$ or $R^5$ is a $C_{(1-8)}$ alkyl radical, while the sum of $R^4$ and $R^5$ is a total of $C_{(2-18)}$ carbon atoms.

Radicals included by R, are for example, phenyl, tolyl, xylyl, naphthyl, chlorophenyl, bromonaphthyl, etc., and alkyl radicals such as methyl, ethyl, propyl, etc. Radicals included by $R^1$ are the aforementioned aromatic radicals, such as phenylene, tolylene, naphthylene, and $R^1$ more particularly includes

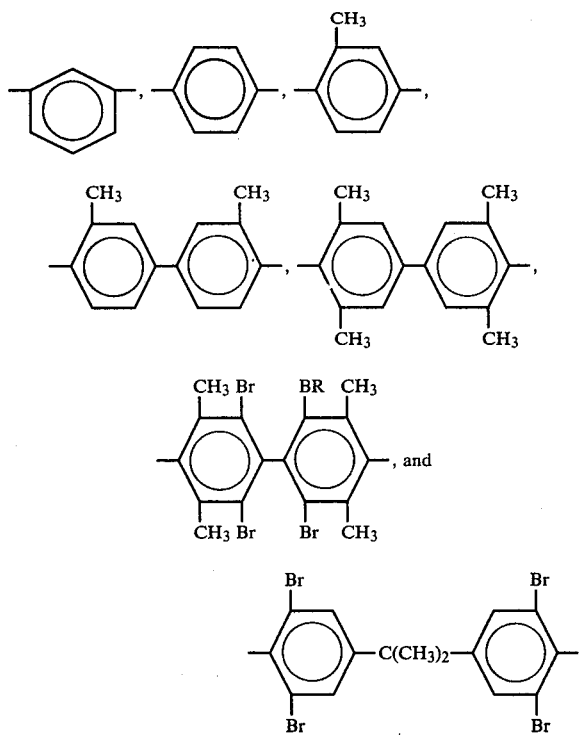

and divalent organic radicals of the general formula,

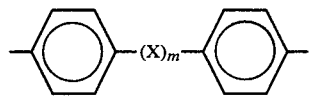

where X is a member selected from the class consisting of divalent radicals of the formula,

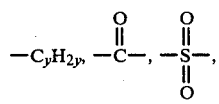

—O— and —S—, where m is 0 or 1, y is a whole number from 1 to 5.

M is more particularly sodium, potassium, lithium, rubidium, etc.; counter ions included by formula (4) are, for example, fluoride, bromide, chloride, methanesulfonate, p-toluenesulfonate, nitrite, sulfate, acetate, etc.

Included by the substituted phthalimides of formula (2) are for example, 4-nitro-N-phenylphthalimide; 3-nitro-N-phenylphthalimide;
4-nitro-N-methylphthalimide; 3-nitro-N-methylphthalimide;
4-fluoro-N-methylphthalimide; 4-fluoro-N-methylphthalimide;
4-chloro-N-methylphthalimide; 3-chloro-N-methylphthalimide, etc.

These substituted phthalimides can be made by standard procedures, such as effecting reaction between substantially equal moles of the corresponding phthalic anhydride and an organic amine in the presence of refluxing acetic acid. Included by the organic amines which can be used, are, for example, aniline, toluidene, etc., methylamine, ethylamine, etc.

Some of the alkylaminopyridines of formula (4) which can be used as phase transfer catalysts are, for example,

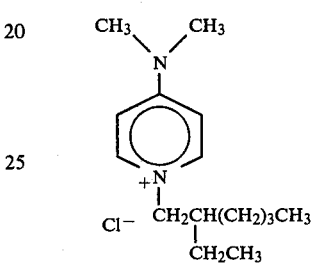

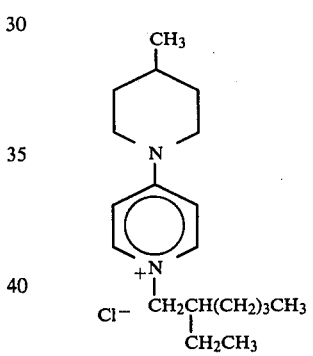

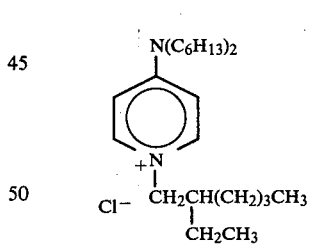

The N-2 branched alkyldiorganoaminopyridinium salts of formula (4) can be made by alkylating diorganoaminopyridines which can be made by reacting 4-hydroxypyridine with phosphorous pentoxide and a diorganoamine at 200° C. to 300° C., for example, 250° C. as shown by the following equation:

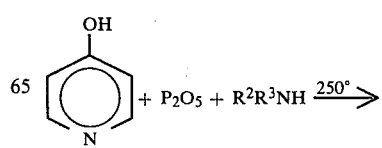

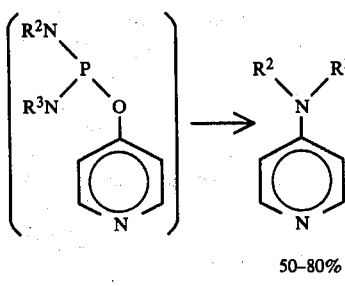

50-80% where R² and R³ are as previously defined.

The alkylation of the above diorganoaminopyridines can be achieved in a straight forward manner utilizing such reagents as isobutylbromide, 2-ethylhexylbromide, etc., at ambient temperatures in an inert organic solvent, for example, chloroform or toluene. Reaction with such branched alkyl compounds, as well as the corresponding tosylate or mesylate can be facilitated by using higher temperatures such as refluxing toluene, or temperatures up to about 150° C.

The alkali metal salts of formula (3) can be made by various procedures, including the flash evaporation of bisphenoxide alkali metal salt hydrate or an aqueous slurry thereof, as shown by U.S. Pat. No. 4,202,993, Takekoshi, or by azeotroping water from an aqueous mixture of bisphenoxide alkali metal salt and toluene as shown by Williams et al U.S. Pat. No. 4,257,953. Additional procedures are shown in White U.S. Pat. No. 3,852,242, assigned to the same assignee as the present invention.

Some of the alkali metal salts of the above-described alkali phenoxides of formula (3) are sodium and potassium salt phenols, such as phenol, cresol, naphthol, etc.; dihydric phenols, for example, 2,2-bis(2-hydroxyphenyl)propane;
2,4'-dihydroxydiphenylmethane;
bis(2-hydroxyphenyl)methane;
2,2-bis(4-hydroxyphenyl)propane, hereinafter identified as "bisphenol-A" or "BPA;"
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone; and
4,4'-dihydroxydiphenylether.

In order that those skilled in the art will be better able to practice the invention, the following examples are given by way of illustration and not by way of limitation. All parts are by weight.

EXAMPLE 1

A mixture of 12.217 grams of dimethylaminopyridine, 20.833 grams of 2-ethylhexylmethane sulfonate was stirred and heated at 110° C. for 1 hour. There was added to the resulting mixture 25 grams of toluene and the solution was refluxed for an additional hour. Toluene was then removed from the mixture under reduced pressure and the resulting crude mesylate salts were washed with hexane. The mesylate salts were then dissolved in methylene chloride and washed twice with a saturated sodium chloride solution. Methylene chloride was then removed under reduced pressure from the resulting product. There was obtained a 31.728 grams of a product having a melting point of 189°–190° C. Based on method of preparation, the product was N-2-ethylhexyldimethylaminopyridine chloride. Its identity was further confirmed by its NMR spectrum: 0.7–1.1 (m, 6H, methyl groups of alkyl chain), 1.3–2.1 (m, 9H, methylenes and methine of alkyl chain), 3.31 (s, 6H, dimethylamino group), 4.25 (d, J=7.5 Hz, 2H, methylene adj to N of pyridine), 7.20 (d, J=7 Hz, 2H, 3- and 5-pyridyl protons), and 8.60 (d, J=7 Hz, 2H, 2- and 6-pyridyl protons). The compound has ir absorptions at 2923 (C—H), 1648 (C=N), and 1563 (C=C) cm$^{-1}$.

EXAMPLE 2

Following the procedure of Example 1, a mixture of 35.25 grams of 4-methylpiperidinylpyridine, and 43.73 grams of 2-ethylhexylmethane sulfonate resulted in the production of 60.83 grams of N-2-ethylhexyl-4-methyl-piperidinylaminopyridine chloride having a melting point of 263°–264° C. The identity of the 4-methylpiperidinylaminopyridine salt was further confirmed by its NMR spectrum: 0.7–1.15 ppm (m, 9H, methyl groups), 1.2–2.15 (m, 14H, alkyl methylenes and methines), 3.22 (broad t, J=11 Hz, 2H, equatorial protons adj to nitrogen on piperidine), 415–4.45 (d superimposed on m, J=7 Hz, 4H, methylene adj to pyridine N, axial protons adj to N on piperidine ring), 7.41 (d, J=7 Hz, 2H, 3- and 5-pyridyl protons), and 8.60 (d, J=7 Hz, 2- and 6-pyridyl protons). The compound has a UV max at 295 nm, with an extinction coeff. of 22,500. The ir has absorptions at 2924 (C—H), 1647 (C=N), and 1556 C=C) cm$^{-1}$.

EXAMPLE 3

A mixture of 2.0 mmoles of 4-nitro-N-methylphthalimide, 0.013 grams of N-2-ethylhexyl-4-methyl-piperidinylaminopyridine chloride and 102 milligrams of fluorenone (internal standard) was dried in an air oven at 140° C. for 1 hour. The resulting mixture was allowed to cool under sealed conditions to ambient temperatures in a drybox. There was then added 1.0 mmole of the disodium salt of bisphenol-A to the resulting mixture and the resulting mixture was then sealed and removed from the drybox. Toluene which had been distilled from sodium was added to the resulting mixture under a stream of nitrogen and the resulting mixture was then heated under sealed conditions from 1–2 hours. A crude reaction product was allowed to cool and diluted with chloroform. The solution was analyzed by high pressure liquid chromatography on a Dupont CN column eluting with THF/isooctane. There was obtained a 94% yield of 2,2-bis[4-(N-phenylphthalimide-4-oxy)phenyl]propane. A 96% yield of the aforementioned bisimide was obtained following the same procedure using the N-2-ethylhexylpyridinium salt of Example 2.

EXAMPLE 4

A study was conducted to determine the stability of various phase transfer catalysts by contacting the catalyst with a mixture of the disodium salt of bisphenol-A and toluene. A vial containing 1.00 mmole of phase transfer catalyst and 1.00 mmole of the disodium salt of bisphenol-A was placed in a vial with toluene. The vial was sealed under substantially anhydrous conditions and heated for a certain time at a particular temperature. At the end of the reaction the vial was allowed to cool and its contents were quenched with water and extracted into methylene chloride. NMR analysis using tetrachlorobenzene as an internal standard provided a measure of the amount of catalyst remaining. Assuming a first order reaction of the catalyst, the half-life of the phase transfer catalyst was determined from the decomposition data. The following results were obtained, where t½ is the half-life of the catalyst, TBABr is tetrabutylammonium bromide, N-neopentyl-4-N',N'-dihexylaminopyridinium bromide is NPDHAPB, N-2-ethylhexyl, 4-methylpiperidinylperidinium chloride is EHMPPC AND butyldimethylaminopyridinium chloride is BDMPC.

| Catalyst | t½ |
|---|---|
| TBABr | 8 min |
| NPDHAPB | 12 hr |
| EHMPPC | 11 hr |
| BDMPC | 2 hr |
| EHDMPC | 8 hr |

The above results show that the branched alkyldiorganoaminopyridinium salts of the present invention possess superior stability as phase transfer catalysts for bisimide formation compared to the tetrabutylammonium bromide salts of the prior art. In addition, the half-lives of 8 hours and 11 hours are substantially equivalent to the neopentyldibutylaminopyridinium bromide of the copending application of Brunelle et al, while being significantly better than the butyldimethylaminopyridinium chloride of Brunelle et al, exhibiting a half-life of only 2 hours.

Although the above examples are directed to only a few of the very many variables which can be used in the production of the N-branched alkyl dialkylpyridinium salts of the present invention, it should be understood that the present invention includes a much greater variety of such phase transfer catalysts as shown by the description preceeding these examples.

What we claim as new and desire to secure by Letters Patent of the United States is:

1. A N-2-branched alkyldiorganoaminopyridinium salt of the formula,

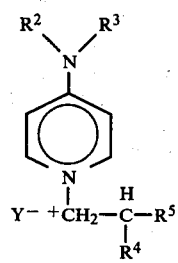

where $R^2$ and $R^3$ are monovalent or divalent organo radicals selected from $C_{(1-13)}$ hydrocarbon radicals and $C_{(1-13)}$ substituted hydrocarbon radicals and $C_{(1-8)}$ divalent alkylene radicals which together can be part of a cyclic structure forming a $C_{(4-12)}$ ring, $R^4$ or $R^5$ is a $C_{(1-8)}$ alkyl radical, while the sum of $R^4$ and $R^5$ is a total of $C_{(2-18)}$ carbon atoms.

2. N-2-ethylhexyldimethylaminopyridine chloride.
3. N-2-ethylhexyl-4-methylpiperidinylaminopyridine chloride.
4. N-2-ethylhexyldihexylaminopyridine chloride.

* * * * *

UNITED STATES PATENT AND TRADEMARK OFFICE
CERTIFICATE OF CORRECTION

PATENT NO.   :   4,460,778
DATED        :   July 17, 1984
INVENTOR(S)  :   Daniel J. Brunelle It is certified that error appears in the above-identified patent and that said Letters Patent is hereby corrected as shown below:

Column 3, line 3, after "atoms", insert "and Y is a counter ion.

Column 8, line 33, after "atoms", insert "and Y is a counter ion.

Signed and Sealed this

Second Day of April 1985

[SEAL]

Attest:

DONALD J. QUIGG

Attesting Officer    Acting Commissioner of Patents and Trademarks